US00PP21444P2

(12) United States Plant Patent
O'Connell

(10) Patent No.: US PP21,444 P2
(45) Date of Patent: Nov. 2, 2010

(54) ***ECHEVERIA* PLANT NAMED 'GORGON'S GROTTO'**

(50) Latin Name: ***Echeveria* hybrid**
Varietal Denomination: Gorgon's Grotto

(76) Inventor: Renee O'Connell, 1801 Tierra Libertia, Escondido, CA (US) 92026

( * ) Notice: Subject to any disclaimer, the term of this patent is extended or adjusted under 35 U.S.C. 154(b) by 0 days.

(21) Appl. No.: 12/455,722

(22) Filed: Jun. 6, 2009

(51) Int. Cl.
*A01H 5/00* (2006.01)

(52) U.S. Cl. ..... Plt./373

(58) Field of Classification Search ..... Plt./373
See application file for complete search history.

*Primary Examiner*—Annette H Para

(57) ABSTRACT

A new and distinct *Echeveria* cultivar named 'Gorgon's Grotto' is disclosed, characterized strongly developed carunculations with carunculated anfractuous leaf apices and highly anfracutuous leaf margins. Foliage is distinctively greyed-purple with large pink caruncles. Plant diameter is unusually large for an *Echeveria*. The new variety is an *Echeveria*, typically produced as a garden or container plant.

1 Drawing Sheet

Figure 1:
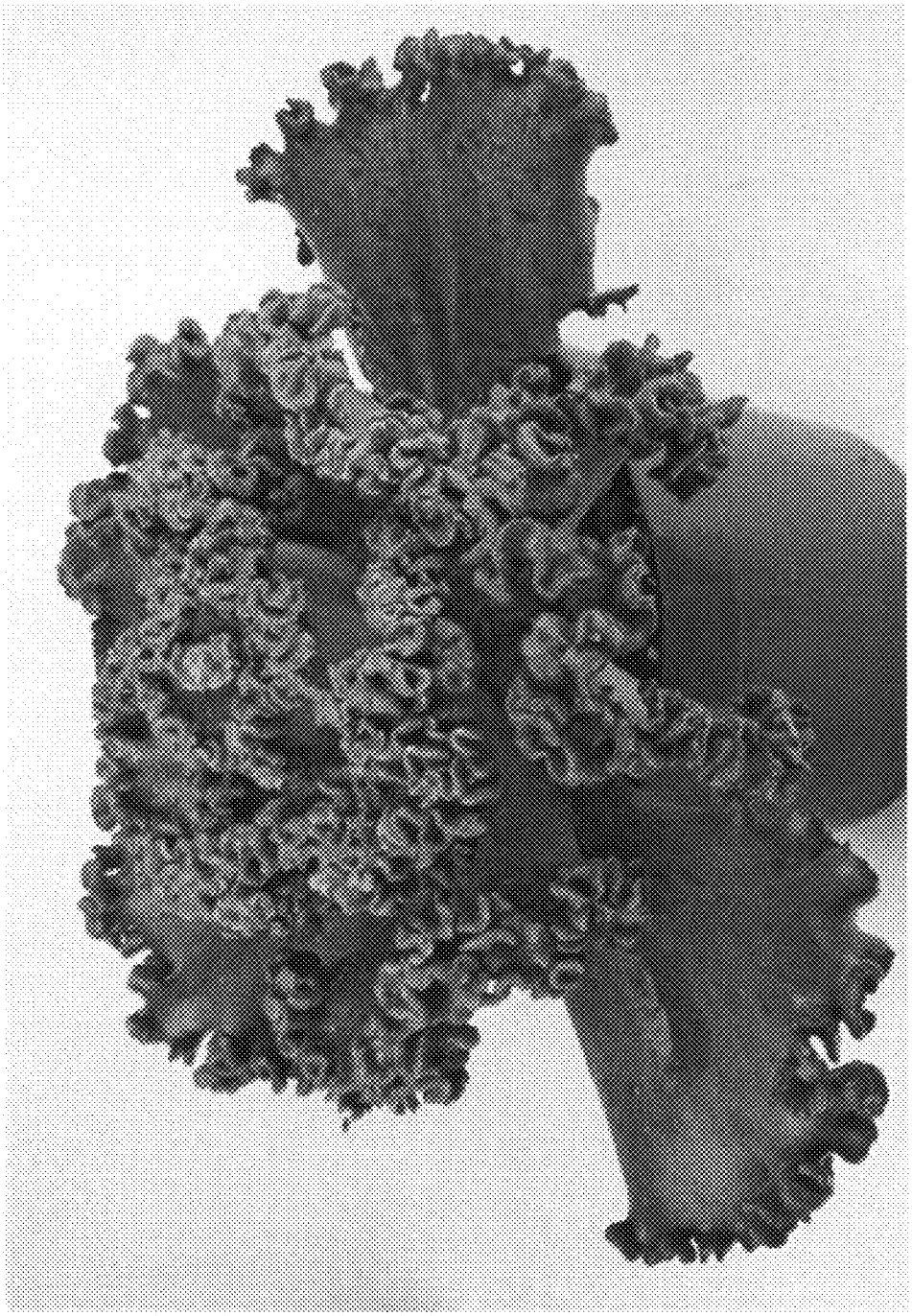

Latin name of the genus and species: *Echeveria* hybrid.
Variety denomination: 'Gorgon's Grotto'.

BACKGROUND OF THE INVENTION

The new cultivar is a product of a planned breeding program. The new variety originated from a cross pollination of the unpatented, proprietary seed parent, *Echeveria* hybrid referred to as 'Enhanced Mauna Loa' with the pollen parent an unpatented proprietary *Echeveria* hybrid referred to as '#3' The crossing was made during November of 2005 in Vista, Calif., at a commercial greenhouse. 'Gorgon's Grotto' was discovered by the inventor, Renee O'Connell, in October 2006, in Vista, Calif. at a commercial greenhouse.

Asexual reproduction of the new cultivar 'Gorgon's Grotto' was first performed in Vista, Calif., at a commercial greenhouse by vegetative leaf cuttings in October 2006. 'Gorgon's Grotto' has since produced several generations and has shown that the unique features of this cultivar are stable and reproduced true to type.

SUMMARY OF THE INVENTION

The cultivar 'Gorgon's Grotto' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Gorgon's Grotto.' These characteristics in combination distinguish 'Gorgon's Grotto' as a new and distinct *Echeveria* cultivar:

1. Strongly developed carunculations with carunculated anfractuous leaf apices.
2. Highly anfracutuous leaf margins.
3. Distinctive greyed-purple foliage with large pink caruncles.
4. Unusually large plant diameter for an *Echeveria.*

PARENTAL COMPARISON

Plants of the new cultivar 'Gorgon's Grotto' are similar to the seed parent 'Enhanced Mauna Loa' in most horticultural characteristics. However, 'Gorgon's Grotto' exhibits unusual, highly anfractuous leaf margins not seen on the seed parent. Additionally, plants of 'Gorgon's Grotto' are larger than the seed parent, and have a different foliage color.

Plants of the new cultivar 'Gorgon's Grotto' are similar to the pollen parent '#3' in most horticultural characteristics. However, 'Gorgon's Grotto' shows better resistance to typical diseases and pests of *Echeveria* than exhibited by *Echeveria* hybrid '#3.' Additionally, foliage of 'Gorgon's Grotto' exhibits margins that are much more anfractuous than *Echeveria* '#3.' Gorgon's Grotto also has a different foliage color and different plant shape than *Echeveria* '#3'.

COMMERCIAL COMPARISON

'Gorgon's Grotto' can be compared to the unpatented commercial variety *Echeveria* 'Barbillion.' Plants of *Echeveria* 'Barbillion' are similar to plants of 'Gorgon's Grotto' in most horticultural characteristics. However, 'Gorgon's Grotto' grows larger, and has an overall different foliage color than 'Barbillion.' Additionally, 'Gorgon's Grotto' produces much more anfractuous margins than Barbillion, and has anfractuous carunculated apices, not produced by 'Barbillion'.

'Gorgon's Grotto' can also be compared to the unpatented commercial variety *Echeveria* 'Cameo.' Plants of *Echeveria* 'Cameo' are similar to plants of 'Gorgon's Grotto' in most horticultural characteristics. However, 'Gorgon's Grotto' does not fade in foliage coloration with age, as is typical of 'Cameo.' Additionally, the foliage of 'Gorgon's Grotto' has a many more leaf carunculations with complex formation than the foliage of 'Cameo.' Overall foliage coloration of 'Gorgon's Grotto' is also greyed-purple, compared to green-blue of 'Cameo'.

BRIEF DESCRIPTION OF THE PHOTOGRAPH

The accompanying photograph in FIG. 1 illustrates in full color a typical plant of 'Gorgon's Grotto' grown outdoors in Vista, Calif. This plant is approximately 10 months old, shown in a 6 inch pot. The photograph was taken using conventional techniques and although colors may appear different from actual colors due to light reflectance it is as accurate as possible by conventional photographic techniques.

DETAILED BOTANICAL DESCRIPTION

In the following description, color references are made to the Panton Process Color System Guide, except where general terms of ordinary dictionary significance are used. The following observations and measurements describe 'Gorgon's Grotto' plants in a commercial greenhouse in Vista, Calif. Temperatures ranged from −1° C. to 29° C. night and day. No artificial light, photoperiodic treatments or chemical treatments were given to the plants. Natural light conditions were approximately 2500 to 4000 fc of light. Measurements and numerical values represent averages of typical plant types.

Botanical classification: *Echeveria* hybrid 'Gorgon's Grotto'.

Age of the plant described: Approximately 5 months.

PROPAGATION

Time to initiate roots: About 25 days at approximately 21° C.

Root description: Fibrous.

Propagation method: Vegetative leaf cuttings.

PLANT

Growth habit: Rosulate, sessile, rarely branching, succulent.

Container size: 6 inch.

Height: Approximately 17 cm to top of highest leaf.

Plant spread: Approximately 29 cm.

Growth rate: Moderate.

Branching characteristics: Rarely.

FOLIAGE

Leaf:

*Arrangement.*—Rosulate.

*Average length.*—Approximately 13 cm.

*Widest width.*—Approximately 10 cm.

*Width at base.*—Approximately 2.75 cm.

*Shape of blade.*—Spatulate.

*Apex.*—Anfractuous.

*Base.*—Rounded.

*Margin.*—Exceedingly crenulate, anfractuous.

*Texture of top surface.*—Glabrous, pruinose, caruncule.

*Texture of bottom surface.*—Glabrous, pruinose.

*Quantity of leaves per plant.*—Approximately 20.

*Color.*—Young foliage upper side: Near S 256-7 Pantone. Young foliage, margin: Near S 286-6 to S 118-6 Pantone. Young foliage, caruncle: Near S 286-6 and S 286-7 Pantone. Young foliage under side: Near S 256-7 Pantone. Mature foliage upper side: Near S 137-5 and S 135-4 Pantone. Mature foliage, margin: Near S 140-1 Pantone. Mature foliage upper side, where pruinose covering removed: Near S 140-2 Pantone. Mature foliage under side: Near S 329-6 green overlaid by S 140-6 Pantone.

*Venation.*—Type: Parallel. Venation color upper side: Indistinguishable from overall foliage color. Venation color under side: Indistinguishable from overall foliage color.

FLOWER

Flowering: Flowering has not been observed to date in the new variety.

OTHER CHARACTERISTICS

Fruits and seeds: Not observed to date.

Temperature tolerance: Tolerates temperatures from approximately −2° C. to 32° C.

Disease/pest resistance: Neither resistance nor susceptibility to normal diseases and pests of *Echeveria* has been observed.

Drought tolerance: Tolerates at least 2 weeks of high temperatures without supplemental water, showing no serious damage to plant.

What is claimed is:

1. A new and distinct cultivar of *Echeveria* plant named 'Gorgon's Grotto' as herein illustrated and described.

* * * * *